US 6,413,552 B1
Jul. 2, 2002

(54) TOPICALLY APPLIED CREATINE CONTAINING COMPOSITION

(76) Inventor: David M. Stoll, 9735 Wilshire Blvd. Suite 418, Beverly Hills, CA (US) 90212

( * ) Notice: Subject to any disclaimer, the term of this patent is extended or adjusted under 35 U.S.C. 154(b) by 0 days.

(21) Appl. No.: 09/941,415

(22) Filed: Aug. 28, 2001

Related U.S. Application Data

(63) Continuation-in-part of application No. 09/723,087, filed on Nov. 27, 2000, now abandoned.

(51) Int. Cl.[7] ............................................... A61K 35/78
(52) U.S. Cl. ........................ 424/728; 424/497; 514/565
(58) Field of Search ................................ 424/728, 497; 514/565

(56) References Cited

U.S. PATENT DOCUMENTS 5,908,864 A * 6/1999 Casey
5,973,005 A * 10/1999 D'Amelio, Sr. et al.
6,242,491 B1 * 6/2000 Kaddurah-Daouk
6,274,161 B1 * 8/2001 Howard et al.

FOREIGN PATENT DOCUMENTS

JP 2000247866 * 9/2000
WO WO 96/33707 * 10/1996

* cited by examiner

Primary Examiner—Christopher R. Tate
(74) Attorney, Agent, or Firm—Norton R. Townsley; Belasco Jacobs & Townsley, LLP

(57) ABSTRACT

The present invention is a stable topical creatine application suitable for absorption directly through the skin into the underlying muscle without traveling through the blood system for the purpose of increasing muscle energy. It is created by combining creatine with phosphoric acid in a cosmetically elegant vehicle suitable for topical use. Chondroitin sulfate and glucosamine can also be added. Topical creatine avoids the side effects of oral creatine supplements.

12 Claims, No Drawings

TOPICALLY APPLIED CREATINE CONTAINING COMPOSITION

CROSS REFERENCE

This application is a continuation-in-part of U.S. patent application Ser. No. 09/723,087 filed Nov. 27, 2000, now abandoned.

BACKGROUND OF THE INVENTION

The present invention relates to the field of muscle stimulation and more particularly to enhancing the production of the energy used to cause contractions and expansions in the muscles of mammals.

Creatine is an important source of providing energy to muscles through its role in adenosine triphosphate (ATP) formation. ATP is the fuel source for muscle contraction. It is formed when adenosine diphosphate (ADP), adds another phosphate group to form ATP. Creatine provides the source for replacing the phosphate group to convert ADP to ATP. As such, it is an integral part of the muscle contraction and expansion process. The more creatine available to muscles, the more ADP can be converted to ATP for use by those muscles. Therefore, for persons involved in strenuous physical activities, such as athletes, a constant source of creatine is vital in order to maintain muscle energy levels.

Creatine is a popular nutritional supplement useful as an energy source for muscles. Chemically, creatine is N-methyl-N-guanylglycine. Creatine is biosynthesized through the transamidination and transmethylation of the amino acids glycine, arginine and methionine.

Creatine is available from several food sources. However, athletes and others wishing to maintain a high level of creatine in their muscles have popularized oral creatine supplements in recent years. These have taken the form of creatine powders, pills, gels, and drinks. Unfortunately, each of these has their drawbacks. A topically applied creatine product holds several advantages over creatine taken orally. Side effects of orally administered creatine are common, including diarrhea, abdominal cramping, flatulence and nausea. One study (Sahelian, R. et al Creatine: Nature's Muscle Builder, 1997) revealed that 38% of men and 25% of women who took oral creatine supplements experienced side effects.

Creatine powders need to be mixed with a liquid and ingested immediately in order to prevent the creatine from being converted to creatinine (an inactive compound) by the liquid. The process of mixing the powder and the liquid is often quite messy. Other preparations such as consumable pills and gels may have a bad taste. Drinks need refrigeration in order to keep the creatine stable in liquid form.

A topically applied creatine product would not have the systemic side effects, mess, inconvenience, and bad taste often associated with orally administered creatine products. In addition, topically applied creatine could be used to augment oral creatine or to potentially reduce the orally ingested dosage.

One of the limitations of using a creatine product is its low solubility in water (1 g in 75 ml). Also, creatine converts to its inactive form, creatinine, at a greater rate when it is mixed with water, alcohol or any other water soluble liquid. Oral creatine gels and liquids have been previously described, but their constitution would render them unfit for topical use because they would be either too sticky, too irritating, or unsuccessful in penetrating the skin. Additionally, none of the currently patented oral creatine products have claimed a topical use.

The invention encompasses a topically applied liquid, gel, cream, ointment, paste, powder, shampoo, solution, lotion, patch, or spray containing stable creatine useful in enhancing muscle strength and energy without traveling through the user's blood stream to the muscle.

U.S. Pat. No. 5,612,375 discloses a process for producing a healthy or nutritious beverage comprising creatine as a main ingredient, in which the effect of creatine is not lost during preservation, and the beverage can be prepared at low cost. A process for producing a creatine beverage comprising the steps of: heating water rendered weakly alkaline; adding from 1 to 3 grams per 100 cc of the heated water, of crystalline creatine powder to the heated water; dissolving the creatine powder by stirring to form a creatine aqueous solution; and adding an additive to the creatine aqueous solution for improving nutrition or palatability, and sterilizing the creatine aqueous solution to obtain a creatine beverage having a pH value of 7 to 10. This invention can be distinguished from the present invention because it covers a beverage containing creatine and the process for producing the beverage and not a process for making a stable topical creatine application suitable for absorption directly through the skin into the underlying muscle without traveling through the blood system eliminating the typical creatine side effects like the present invention.

U.S. Pat. No. 5,773,473 discloses a creatine supplement which contains a combination of creatine and propylene glycol. The supplement preferably contains from about 25–50% creatine and from about 50–75% propylene glycol. The propylene glycol not only makes the supplement more bioavailable than conventional creatine supplements, but also decreases the incidence of side effects. This invention can be distinguished from the present invention because it covers an orally introduced creatine dietary supplement and the process for producing the beverage and not a process for making a stable topical creatine application suitable for absorption directly through the skin into the underlying muscle without traveling through the blood system like the present invention.

U.S. Pat. No. 5,886,042 discloses preventive as well as therapeutic treatment to alleviate cosmetic conditions and symptoms of dermatologic disorders with amphoteric compositions containing alpha hydroxyacids, alpha ketoacids, related compounds or polymeric forms of hydroxyacids. The cosmetic conditions and the dermatologic disorders in which the amphoteric compositions and the polymeric compounds may be useful include dry skin, dandruff, acne, keratoses, psoriasis, eczema, pruritus, age spots, lentigines, melasmas, wrinkles, warts, blemished skin, hyperpigmented skin, kyperkeratotic skin, inflammatory dermatoses, skin changes associated with aging, and skin requiring cleansers. This invention can be distinguished from the present invention because it covers a topical treatment for skin disorders associated with keratinization or inflamation and not a process for making a stable topical creatine application suitable for absorption directly through the skin into the underlying muscle to increase the amount of energy available to the muscle energy.

U.S. Pat. No. 5,908,864 discloses a nutritional gel containing creatine and the method of producing the creatine gel. The creatine gel is made by cross linking maltodextrin and a modified starch through an aqueous endothermal reaction at a temperature of approximately 90 degrees Celsius. A buffering agent, such as potassium phosphate, is added to the gel to maintain a pH value at approximately 7.0. The gel is then cooled and creatine is added. Next, the gel is stabilized bacteriologically by adding a preservative, such as potassium sorbate to the gel. This invention can be distinguished from the present invention because it covers an orally introduced creatine dietary supplement and the process for producing it and not a process for making a stable topical creatine application suitable for absorption directly through the skin into the underlying muscle without traveling through the blood system like the present invention.

U.S. Pat. No. 5,973,005 discloses a stable aqueous solution of creatine acid sulfate which provides a source of creatine to an animal when taken orally. The aqueous solution of creatine acid sulfate (after neutralization and buffering) has a pH of about 7.2 to about 7.8 and is stable for at least six months at room temperature. The creatine acid sulfate is produced by adding creatine monohydrate to a sulfuric acid solution in a stoichiometric amount to result in creatine acid sulfate having a pH initially of 2.0–3.0. The resulting creatine acid sulfate is diluted with water and neutralized to raise the pH and avoid the formation of creatinine. The resulting creatine acid sulfate solution preferably contains a buffering and neutralizing agent such as tribasic potassium phosphate which forms mono- and dibasic potassium phosphates by interaction with the hydrogen ions liberated from the acid sulfate. The aqueous solution can be combined with a sweetener, electrolyte and carbohydrate source to produce a stable drink for providing a source of creatine to an animal in need thereof. An effective amount of glycerol is preferably added to enhance absorption of the creatine through the intestinal wall into the bloodstream and eventually to the needy skeletal muscles. This invention can be distinguished from the present invention because it covers an orally introduced creatine dietary supplement and the process for it and not a process for making a stable topical creatine application suitable for absorption directly through the skin into the underlying muscle without traveling through the blood system like the present invention.

U.S. Pat. No. 5,973,199 discloses hydrosoluble organic salts of creatine. The salts are useful in the dietetic and food industry. Similarly, this invention can be distinguished from the present invention because it covers an orally introduced creatine dietary supplement and the process for producing it and not a process for making a stable topical creatine application suitable for absorption directly through the skin into the underlying muscle without traveling through the blood system like the present invention.

International Patent Application No. WO 96/33707 describes an invention of topically applied creatine in a multitude of bases such as creams, ointments, lotions, and alcohol for use as a spray. This application states that creatine can be put into long-chain lipoacids or long-chain (between 10 and 20 carbon atoms) alcohols and ester derivatives of those alcohols. Although this patent makes it sound easy to put creatine into solution, it is not. When creatine is placed into an alcohol solution it becomes unstable and precipitates out forming creatinine.

Development of a stable topical creatine application suitable for absorption directly through the skin into the underlying muscle without traveling through the blood system represents a great improvement in the field of sports medicine and satisfies a long felt need for creatine in a cutaneously elegant form that will maintain clinically efficacy while not being degraded to creatinine, without the mess and side effects.

SUMMARY OF THE INVENTION

The present invention is a topical application of creatine in a vehicle suitable for absorption directly through the skin into the underlying muscle without traveling through the blood system. The topical application includes ingredients with the functions of solvent, carrier for creatine, pH adjuster, amino acid, energy producer, skin conditioning agent, aromatic, skin smoothing agent, skin toning agent, buffer agent, preservative, and colorant.

Embodiments of the present invention could take the form of any of the following; a liquid, a gel, a cream, an ointment, a paste, a powder, a shampoo, a lotion, a patch, or a spray. The invention can also be impregnated into clothing such as hosiery or sportswear. Then when a person exercises their sweat leaches the creatine compound out of the clothing and into their skin. In addition, other ingredients such as amino acids, vitamins, minerals, carbohydrates, liposomes or penetration enhancers may be added.

Another embodiment of this invention includes the addition of glucosamine sulfate and chondroitin for patients who have evidence of osteoarthritis and other causes of pain ruled out.

DETAILED DESCRIPTION OF THE PREFERRED EMBODIMENT

The preferred embodiment of the invention is a spray with the following formulation:

| Concentration | Ingredient | Function |
| --- | --- | --- |
| 25–30% | Water | solvent |
| 45–50% | Ethanol | solvent |
| 2–5% | Ethoxydiglycol | Carrier for creatine |
| 2–5% | Triethanolamine | pH adjuster (neutralizer) |
| 0.5–2% | Creatine monohydrate | Amino acid energy |
| 0.10–0.5% | Ginseng extract | Energy producer |
| 0.10–0.5% | Dimethicone copolyol | Skin conditioning agent |
| 0.05–0.5% | Lavender oil | aromatic |
| 0.05–0.5% | Bergamont oil | aromatic |
| 0.05–0.25% | Sage extract | Skin smoothing agent |
| 0.05–0.25% | Elder flower | Skin smoothing agent |
| 0.05–0.25% | Chamomile | Skin smoothing agent |
| 0.05–0.25% | Witch hazel extract | Skin toning agent |
| 0.10–0.5% | Phosphoric acid | Buffer agent |
| 0.10–0.5% | Phenoxyethanol | preservative |
| 0.05–0.25% | Methylparaben | preservative |
| 0.05–0.25% | Propylparaben | preservative |
| 0.05–0.25% | Butylparaben | preservative |
| 0.05–0.25% | Ethylparaben | preservative |
| 0.01–0.1% | Food Drug and Cosmetic Act (FD&C) blue #1 | colorant |
| 0.01–0.1% | FD&C red #40 | colorant |

The preferred method of preparing the creatine spray includes the following steps. Blending deionized water with phosphoric acid and creatine to create a clear and uniform slurry. Blending a neutralizer with deionized water, dimethicone copolyol, ginseng and a combination of herbal extracts to achieve a skin soothing conditioner. Combining the slurry with the conditioner to create a stable creatine solution of pH 7.8. Blending ethanol and ethoxydiglycol into the stable creatine solution to form a fast drying, quickly absorbing stable creatine solution. This method of preparation is a novel way of putting creatine in solution without allowing conversion of creatine to creatinine. Testing has shown this method keeps the creatine viable in the liquid solvent for at least 6 months.

A novel discovery of the current invention relates to its absorption. Ingredients such as corticosteroids or sun screens when applied over large skin surfaces are absorbed into the systemic circulation and exhibit demonstrable plasma levels of those respective ingredients. As a small molecular weight (134) molecule, creatine should be rapidly absorbed into the systemic circulation, especially upon being applied over the entire skin surface of the body. However, studies demonstrate that no creatine was detected in the plasma of the volunteers 1 hour after application of the above formulation on the entire skin surface. This indicates that the easily absorbed creatine is being incorporated directly into the muscle without having to pass through the blood circulation. This affords easy bioavailability of the creatine to muscles. The topically applied creatine is absorbed and acts directly on the target organ similar to methylsalicylate in arthritis creams and aminophylline in thigh creams.

The alternate embodiment includes 0.25–3% chondroitin sulfate, or 0.25–3% glucosamine, or 0.25–3% chondroitin sulfate and 0.25–3% glucosamine.

EXPERIMENTS

A. Several volunteers had their blood drawn to determine baseline levels of creatine, serum glutamate oxalacetate transaminase (SGOT), serum glutamate pyruvate transaminase (SGPT) and bilirubin. The volunteers then applied the creatine 1% spray described herein, all over their entire skin surface. One hour later, their blood was again tested for plasma levels of creatine, SGOT, SGPT and bilirubin. The results were as follows:

| Volunteer 1: | |
|---|---|
| Baseline values | 1 hour after application of creatine 1% spray |
| Creatine 0.5 | 0.5 |
| SGOT 25 | 23 |
| SGPT 13 | 15 |
| Bilirubin 0.5 | 0.5 |

| Volunteer 2: | |
|---|---|
| Baseline values | 1 hour after application of creatine 1% spray |
| Creatine 0.8 | 0.8 |
| SGOT 18 | 18 |
| SGPT 15 | 16 |
| Bilirubin 0.5 | 0.5 |

| Volunteer 3: | |
|---|---|
| Baseline values | 1 hour after application of creatine 1% spray |
| Creatine 0.5 | 0.5 |
| SGOT 25 | 22 |
| SGPT 23 | 24 |
| Bilirubin 0.4 | 0.4 |

All 3 volunteers used the creatine spray for 2 weeks before exercising and reported that they felt an increase in muscle energy by the end of the 2-week period.

B. A study was conducted on the invention at Alabama A&M University. There were seven participants. Three participants used placebo and four used the invention. Each applied the spray to their skin daily before working out. After two weeks they evaluated the product. The three who used placebo had no side effects and no good effects. Of the four who used the invention, none had any side effects and three felt that they experienced some increase in energy.

The topically applied creatine containing composition has been described with reference to a particular embodiment. Other modifications and enhancements can be made without departing from the spirit and scope of the claims that follow.

What is claimed is:

1. A method of preparing a topical application of creatine comprising the steps of:

blending deionized water with phosphoric acid and creatine to create a clear and uniform slurry;

blending a neutralizer with deionized water, dimethicone copolyol, ginseng extract and one or more other herbal extracts to achieve a skin soothing conditioner;

combining said slurry with said conditioner to create a stable creatine solution of pH 7.8; and blending alcohol and ethoxydiglycol into said stable creatine solution to form a fast drying, quickly absorbing, stable solution.

2. A method of preparing a topical application of creatine according to claim 1 further comprising the step of incorporating said solution into a gel.

3. A method of preparing a topical application of creatine according to claim 1 further comprising the step of incorporating said solution into a cream.

4. A method of preparing a topical application of creatine according to claim 1 further comprising the step of incorporating said solution in to an ointment.

5. A method of preparing a topical application of creatine according to claim 1 further comprising the step of incorporating said solution into a paste.

6. A method of preparing a topical application of creatine according to claim 1 further comprising the step of incorporating said solution into a lotion.

7. A method of preparing a topical application of creatine according to claim 1 further comprising the step of incorporating said solution a patch.

8. A method of preparing a topical application of creatine according to claim 1 further comprising the step of incorporating said solution a spray.

9. A method of preparing a topical application of creatine according to claim 1 further comprising the step of impregnating said solution into exercise clothing.

10. A method of preparing a topical application of creatine according to claim 1 further comprising the step of adding 0.25–3.00% chondroitin sulfate to said stable solution.

11. A method of preparing a topical application of creatine according to claim 1 further comprising the step of adding 0.25–3.00% glucosamine to said stable solution.

12. A method of preparing a topical application of creatine according to claim 1 further comprising the step of adding 0.25–3.00% chondroitin sulfate and 0.25–3.00% glucosamine to said stable solution.

* * * * *